United States Patent [19]

Chou et al.

[11] Patent Number: 4,616,080

[45] Date of Patent: Oct. 7, 1986

[54] SIMPLIFIED PROCESS OF FORMING CRYSTALLINE CEFTAZIDIME PENTAHYDRATE

[75] Inventors: Ta-Sen Chou, Indianapolis; Robert E. Lakin, Brownsburg, both of Ind.

[73] Assignee: Eli Lilly and Company, Indianapolis, Ind.

[21] Appl. No.: 627,321

[22] Filed: Jul. 2, 1984

[51] Int. Cl.$^4$ .................. C07D 501/46; A61K 31/545
[52] U.S. Cl. ..................................... 540/225; 540/222
[58] Field of Search .......................................... 544/25

[56] References Cited

U.S. PATENT DOCUMENTS

| 4,258,041 | 3/1981 | O'Callaghan et al. | 514/202 |
| 4,329,453 | 5/1982 | Brodie et al. | 544/25 |
| 4,467,086 | 8/1984 | Miller | 544/25 |
| 4,537,959 | 8/1985 | Chou | 544/25 |

OTHER PUBLICATIONS

Wiberg "Laboratory Technique in Organic Chemistry", 1960, McGraw-Hill, pp. 179 and 180.

*Primary Examiner*—Donald G. Daus
*Assistant Examiner*—Robert Benson
*Attorney, Agent, or Firm*—William B. Scanlon; Leroy Whitaker

[57] ABSTRACT

Ceftazidime pentahydrate in crystalline form is provided in a one-step process comprising acidic removal of protecting groups from an amino-protected and carboxy-protected ceftazidime, separation of aqueous phase after addition of a water-immiscible organic solvent, and precipitation of pentahydrate by adjusting pH of aqueous phase from about 3.5 to about 4.5.

6 Claims, No Drawings

SIMPLIFIED PROCESS OF FORMING CRYSTALLINE CEFTAZIDIME PENTAHYDRATE

BACKGROUND OF THE INVENTION

This invention relates to a process for the preparation of an antibiotic in crystalline form. In particular, it relates to a process for the preparation of the antibiotic ceftazidime pentahydrate.

The semi-synthetic cephalosporin antibiotic ceftazidime, chemically named (6R,7R)-7-[(Z)-2-(2-aminothiazol-4-yl)-2-(2-carboxyprop-2-oxyimino)acetamido]-3-(1-pyridiniummethyl)-3-cephem-4-carboxylate, is described in U.S. Pat. No. 4,258,041. A particularly useful pharmaceutical form of ceftazidime is its crystalline pentahydrate which is described by Brody et al. in U.S. Pat. No. 4,329,453. Prior to the present invention, ceftazidime pentahydrate has been obtained with a disalt of ceftazidime, for example, the dihydrochloride salt as described by Brody et al. The dihydrochloride salt of ceftazidime is first prepared and isolated, the salt is dissolved in an aqueous medium which may contain a water-miscible organic solvent, and the pH of the mixture is adjusted to between about 3.3 and 4.0 to form the pentahydrate. The pentahydrate will generally crystallize from the acidic mixture. The disalts of ceftazidime, for example the dihydrochloride salt, are obtained by the acidic removal of an amino-protected and esterified ceftazidime. This intermediate hereinafter referred to as "diblocked ceftazidime" is an intermediate arising in the overall preparation of ceftazidime by the acylation of 7-amino-3-(1-pyridiniummethyl)-3-cephem-4-carboxylate with the diprotected side chain moiety of ceftazidime. A preferred protecting group for the 2-amino group of the 2-aminothiazole ring in the 7-position of ceftazidime is the trityl group, while the carboxy group in the 7-position side chain of ceftazidime is preferably protected by the t-butyl group. Both of these groups are removable under acidic conditions and typically the deblocking step following the acylation comprises the use of formic acid and hydrochloric acid to remove both the trityl group and the t-butyl ester group. In the course of this deblocking, the ceftazidime dihydrochloride salt is formed. Other acid labile protecting groups for the amino group and the carboxy group may be employed instead of the preferred trityl and t-butyl groups.

According to the process of this invention, ceftazidime pentahydrate in crystalline form is obtained directly from the reaction mixture in which the deblocking of the diblocked ceftazidime is carried out. The separate preparation and isolation of a ceftazidime disalt, for example, the dihydrochloride salt, is thus avoided. The process of the invention affords crystalline ceftazidime pentahydrate in quality equal to that provided by the known procedures.

SUMMARY

This invention provides a process for converting diblocked ceftazidime, (6R,7R)-7-[(Z)-2-(2-tritylaminothiazol- 4-yl)-2-(2-t-butyloxycarbonylprop-2-oxyimino)-acetamido]-3-(1-pyridiniummmethyl)-3-cephem-4-carboxy-late, directly to ceftazidime pentahydrate in crystalline form which comprises treating the diblocked ceftazidime intermediate with formic acid and either concentrated hydrochloric acid or 48% hydrobromic acid, filtering the reaction mixture to remove triphenylmethanol, adjusting the pH of the filtered mixture to about 3.0 with base, adding to the reaction mixture a water-immiscible organic solvent, for example, a ketone such as methyl ethyl ketone or an ester such as ethyl acetate, separating the aqueous phase, and adjusting the pH of the aqueous phase to about 3.7 to precipitate crystalline ceftazidime pentahydrate.

The process of this invention thus avoids the necessity of using a previously prepared and isolated salt of ceftazidime, for example, the dihydrochloride salt, in the preparation of ceftazidime pentahydrate.

DETAILED DESCRIPTION

The process of this invention provides an alternative route to crystalline ceftazidime pentahydrate. As was mentioned above, crystalline ceftazidime pentahydrate was obtained with previously prepared and isolated ceftazidime dihydrochloride salt. According to the process of this invention, the crystalline pentahydrate is obtained from the reaction mixture in which ceftazidime is formed by the acidic deprotection of an aminoprotected and carboxy-protected ceftazidime intermediate.

The process of this invention comprises mixing (6R,7R)-[(Z)-2-(2-tritylaminothiazol-4-yl)-2-(2-t-butyloxycarbonylprop-2-oxyimino)acetamido]-3-(1-pyridiniummethyl)-3-cephem-4-carboxylate, hereinafter referred to as diblocked ceftazidime, with 98% formic acid. The solution of the diblocked intermediate in formic acid is then chilled to a temperature between about 5° C. and 20° C. and concentrated hydrochloric acid or concentrated (48%) hydrobromic acid is added to the mixture. When deblocking is complete, the mixture is filtered to remove triphenylmethanol formed with the deblocked trityl group. The pH of the aqueous filtrate is adjusted to about 2.5 to 3.2 with base. A water-immiscible organic solvent selected from the group consisting of ethyl acetate, methyl ethyl ketone, methyl isobutyl ketone, methylene chloride, and pentan-2-one is added. The organic solvent is added to the filtrate in an amount corresponding to between about 2 and 3 times the volume of the aqueous ceftazidime-containing filtrate. In general, larger volumes of organic solvent may be used; however, for reasons of economy the solvent is used in an amount sufficient to form a two-phase system comprising the aqueous layer and the organic layer.

The aqueous layer formed upon addition of the water-immiscible organic solvent is separated and, if necessary, filtered through a filter aid to remove polymeric and other impurities. Trace residual amounts of the organic solvent are removed from the aqueous phase by evaporation for best results. The pH of the aqueous phase is then adjusted to between about 3.5 and about 4.5 to precipitate crystalline ceftazidime pentahydrate. The adjustment in pH is preferably carried out in the cold, for example, at a temperature of about 10° C. to about 15° C. The pentahydrate can be separated by conventional means such as filtration, centrifugation, etc.

Following the acidic deblocking of the amino protecting trityl group and the carboxy-protecting t-butyl group, the pH of the acidic mixture is adjusted to a pH between about 2.5 and about 3.2 with base. Suitable bases which can be used for the pH adjustment include sodium hydroxide, potassium hydroxide, or an alkali metal carbonate or bicarbonate. Preferable sodium hydroxide is used with 6N sodium hydroxide being used to maintain the total volume of the aqueous at a minimum.

The triphenylmethanol formed in the deblocking is preferably removed by filtration as noted above, however; if desired, the filtration may be omitted since the side product triphenylmethanol is solubilized by the later addition of the water immiscible organic solvent.

In carrying out the process, the diblocked ceftazidime is first dissolved in 98% formic acid at about room temperature, the solution is cooled, and the concentrated hydrochloric acid or concentrated hydrobromic acid is added. Alternatively, the diblocked intermediate may be mixed with a mixture of the formic acid and the hydrohalic acid without prior solution in formic acid.

The crystalline pentahydrate provided by the process of this invention is comparable in purity and stability with that obtained with the intermediate crystalline ceftazidime dihydrochloride or dihydrobromide salt.

The following examples further illustrate the manner of carrying out the process of the invention.

EXAMPLE 1

To 40 ml of 98% formic acid were added 18.36 g (18.2 mmole) of (6R,7R)-7-[(Z)2-(2-tritylaminothiazol-4-yl)-2-(2-t-butyloxycarbonylprop-2-oxyimino)acetamido]-3-(1-pyridiniummethyl)-3-cephem-4-carboxylate and after the solution was stirred for 30 minutes and cooled to 10°–15° C., 8.0 ml of concentrated hydrochloric acid were added. The acidified mixture was stirred for 3.5 hours at room temperature and then was cooled and the pH adjusted to 3.0 with 6N NaOH. Ethyl acetate, 100 ml, was added to the mixture and the aqueous layer was separated, washed with 50 ml of ethyl acetate, and evaporated briefly under vacuum to remove residual ethyl acetate. The pH of the aqueous product-containing layer was adjusted to 3.75 with 6N NaOH. The solution was seeded with crystals of ceftazidime pentahydrate and stirred in the cold (13°–15° C.). When crystallization began, the mixture was stored in the refrigerator. The product, crystalline ceftazidime pentahydrate, was collected, washed with 100 ml of cold water and 50 ml of acetone and air dried. There were obtained 8.2 g (67.0% yield, corrected). Karl Fischer water analysis: 12.28%.

EXAMPLE 2

To 200 ml of 98% formic acid were added 91.8 g of the diblocked intermediate and the mixture was stirred at room temperature for 30 minutes. The mixture was cooled to a temperature between 10°–15° C. and 40 ml of concentrated hydrochloric adid were added slowly. The cooling bath was removed and the mixture was stirred for 3.5 hours at room temperature. The reaction mixture was filtered to remove the precipitated triphenylcarbinol and was then treated with cooling with 6.25N sodium hydroxide to adjust the pH to 3.0. Methyl ethyl ketone, 1500 ml, was added to the mixture. After stirring for 10 minutes, the aqueous layer containing the deblocked product in salt form was separated and filtered through celite. The clear filtrate was placed under vacuum to remove residual MEK and the pH of the aqueous solution was adjusted to 3.75 with concentrated hydrochloric acid with cooling at 13°–15° C. The solution was seeded and stirred at 13°–15° C. The product, crystalline ceftazidime pentahydrate, began to crystallize after 40 minutes. The mixture was placed in the refrigerator to complete crystallization. The crystals were collected by filtration and were washed with 500 ml of cold water and with 300 ml of acetone. The crystals were air dried. There were obtained 35.25 g of product. HPLC analysis of the product indicated 82.6% of ceftazidime (anhydrous basis). 58.5% yield, corrected for assay. Karl Fischer water analysis: 12.52%.

EXAMPLE 3

To 2000 ml of 98% formic acid cooled in an ice bath were added 918 g (1 mole) of diblocked ceftazidime, the ice bath was removed, and the mixture was stirred for 0.5 hour to obtain a solution. The solution was cooled to a temperature of about 10°–15° C. and 400 ml of concentrated hydrochloric acid were added to the solution over 15 min. The cooling bath was removed and the lemon yellow solution was stirred for 3.5 hours at room temperature. The reaction mixture was filtered to remove triphenylmethanol and the filter cake was washed on the filter with 500 ml of 98% formic acid. The pH of the clear orange filtrate was adjusted to 3.0 with 6N NaOH at 0°–5° C. Next 15 l of methyl ethyl ketone were added to the filtrate with stirring. After stirring for 15 minutes, the aqueous phase containing the product was separated and briefly evaporated under vacuum at 40° to remove residual organic solvent. The aqueous phase was filtered over celite and the filtrate was cooled to 13°–15° C. The pH of the cold filtrate was adjusted to 3.75 and seed crystals were added. The solution was maintained at about 0° C. for 15 hours. The ceftazidime pentahydrate crystals were filtered off, slurried twice with 1.5 l of cold water and once with 1 l of cold acetone, and air dried at room temperature. There were obtained 383.1 g of the pentahydrate (63.7% yield corrected for HPLC analysis as anhydrous ceftazidime Karl Fischer water analysis: 12.52%.

We claim:

1. In the process for preparing (6R, 7R)-7-[(Z)-2-(2-aminothiazol-4-yl)-2-(2-carboxyprop-2-oxyimino)acetamido]-3-(1-pyridiniummethyl)-3-cephem-4-carboxylate pentahydrate in crystalline form which comprises the steps of (1) mixing (6R, 7R)-7-[(Z)-2-(2-tritylaminothiazol-4-yl)-2-(2-t-butyloxycarbonylprop-2-oxyamino)acetamido]-3-(1-pyridiniummethyl)-3-cephem-4-carboxylate with 98% formic acid and concentrated hydrochloric acid or concentrated hydrobromic acid, (2) isolating the (6R, 7R)-7-[(Z)-2-(2-aminothiazol -4-yl)-2-(2-carboxyprop-2-oxyimino)acetamido]-3-(1-pyridiniummethyl)-3-cephem-4-carboxylic acid dihydrochloride or dihydrobromide, (3) forming an aqueous solution of said dihydrochloride or said dihydrobromide and (4) adjusting the pH of said solution to 3.3 to 4, the improvement which comprises mixing said acid mixture of step 1 with an organic solvent selected from the group consisting of ethyl acetate, methyl ethyl ketone, diethyl ketone, methyl isobutyl ketone, methylene chloride and methyl n-propyl ketone in an amount sufficient to form a 2-phase system; separating the aqueous phase and adjusting the pH of the aqueous phase to between about 3.5 and about 4.5.

2. The process of claim 1 which comprises the further step of separating the crystalline pentahydrate.

3. The process of claim 1 wherein methyl ethyl ketone is used as the water-immiscible solvent.

4. The process of claim 1 wherein ethyl acetate is used as the water-immiscible solvent.

5. The process of claim 1 wherein the pH is adjusted to between about 3.7 and about 3.8.

6. The process of claim 1 wherein the reaction mixture is filtered prior to addition of the water-immiscible solvent.

* * * * *